(12) United States Patent
Laughlin et al.

(10) Patent No.: US 10,987,016 B2
(45) Date of Patent: Apr. 27, 2021

(54) VISUALIZATION SYSTEM FOR DEEP BRAIN STIMULATION

(71) Applicant: The Boeing Company, Chicago, IL (US)

(72) Inventors: Brian Dale Laughlin, Wichita, KS (US); Dane Brian Laughlin, Wichita, KS (US); Madison Lauryn Laughlin, Wichita, KS (US)

(73) Assignee: The Boeing Company, Chicago, IL (US)

( * ) Notice: Subject to any disclaimer, the term of this patent is extended or adjusted under 35 U.S.C. 154(b) by 360 days.

(21) Appl. No.: 15/684,092

(22) Filed: Aug. 23, 2017

(65) Prior Publication Data
US 2019/0059773 A1   Feb. 28, 2019

(51) Int. Cl.
| | |
|---|---|
| *A61N 1/372* | (2006.01) |
| *A61B 5/0482* | (2006.01) |
| *A61N 1/36* | (2006.01) |
| *A61N 1/05* | (2006.01) |
| *A61N 1/18* | (2006.01) |

(Continued)

(52) U.S. Cl.
CPC .......... *A61B 5/0482* (2013.01); *A61B 5/6803* (2013.01); *A61N 1/0484* (2013.01); *A61N 1/0534* (2013.01); *A61N 1/18* (2013.01); *A61N 1/3606* (2013.01); *A61N 1/36025* (2013.01); *A61N 1/37247* (2013.01); *A61B 5/4064* (2013.01); *A61B 34/25* (2016.02); *A61B 2090/365* (2016.02); *A61B 2090/372* (2016.02);

(Continued)

(58) Field of Classification Search
CPC ..................... A61B 2090/365; A61N 1/37247
See application file for complete search history.

(56) References Cited

U.S. PATENT DOCUMENTS 6,061,587 A * 5/2000 Kucharczyk ........ A61M 31/005
600/411
8,239,030 B1   8/2012 Hagedorn et al.
(Continued)

FOREIGN PATENT DOCUMENTS

| EP | 2664356 A1 | 11/2013 |
|---|---|---|
| WO | WO2016139576 A2 | 9/2016 |
| WO | WO2019040315 A1 | 2/2019 |

OTHER PUBLICATIONS

International Search Report and Written Opinion, dated Oct. 31, 2018, regarding Application No. PCT/US2018/046606, 16 pages.

*Primary Examiner* — George R Evanisko
(74) *Attorney, Agent, or Firm* — Yee & Associates, P.C.

(57) ABSTRACT

A system, method, and apparatus for a visualization system for deep brain stimulation. The visualization system comprises a camera system, a display system, and an information analyzer. The information analyzer is configured to display a group of electrodes for the deep brain stimulation on a head of a patient on the display system such that a visualization of the group of electrodes is displayed overlaid on the head of the patient in real time in a position corresponding to an actual position of the group of electrodes in a brain in the head of the patient. An operation of the group of electrodes sending an electrical signal into the head of the patient is displayed in the visualization, enabling visualizing a physical reaction of the patient to the deep brain stimulation in conjunction with the visualization of the operation of the group of electrodes.

24 Claims, 7 Drawing Sheets

(51) Int. Cl.
   *A61B 5/00*    (2006.01)
   *A61N 1/04*    (2006.01)
   *A61B 90/00*   (2016.01)
   *A61B 34/00*   (2016.01)
   *A61B 90/50*   (2016.01)

(52) U.S. Cl.
   CPC ..... *A61B 2090/502* (2016.02); *A61N 1/36067* (2013.01); *A61N 1/372* (2013.01)

(56) References Cited

U.S. PATENT DOCUMENTS

| | | | |
|---|---|---|---|
| 2002/0082498 A1* | 6/2002 | Wendt | G06F 19/3418 600/411 |
| 2003/0179308 A1 | 9/2003 | Zamorano et al. | |
| 2007/0179558 A1 | 8/2007 | Gliner et al. | |
| 2007/0238981 A1 | 10/2007 | Zhu et al. | |
| 2008/0064947 A1* | 3/2008 | Heruth | A61N 1/36128 600/407 |
| 2008/0097187 A1* | 4/2008 | Gielen | G06T 7/0012 600/409 |
| 2009/0287271 A1* | 11/2009 | Blum | A61N 1/37247 607/45 |
| 2010/0268287 A1 | 10/2010 | Celnik | |
| 2011/0172564 A1* | 7/2011 | Drew | A61B 5/061 600/587 |
| 2012/0314919 A1* | 12/2012 | Sparks | G06F 19/321 382/128 |
| 2013/0267838 A1* | 10/2013 | Fronk | A61B 5/066 600/424 |
| 2013/0268019 A1 | 10/2013 | Gupta et al. | |
| 2014/0277284 A1* | 9/2014 | Chen | A61N 1/36132 607/59 |
| 2016/0086380 A1* | 3/2016 | Vayser | G02B 27/0172 345/633 |
| 2016/0235323 A1 | 8/2016 | Tadi et al. | |
| 2016/0249989 A1 | 9/2016 | Devam et al. | |
| 2017/0099479 A1 | 4/2017 | Browd et al. | |
| 2017/0113056 A1 | 4/2017 | Stocco et al. | |
| 2019/0015162 A1* | 1/2019 | Abhari | A61B 34/20 |

* cited by examiner

VISUALIZATION SYSTEM FOR DEEP BRAIN STIMULATION

BACKGROUND INFORMATION

1. Field

The present disclosure relates generally to biomedical systems and, in particular, to a visualization system for deep brain stimulation.

2. Background

As people age, their brains become less efficient at managing the electro-chemical nervous signals it generates, sometimes leading to decreased motor function capabilities. In some extreme cases, such as Essential Tremors and Parkinson's disease, the brain effectively "short circuits" resulting in chronic, uncontrollable, spasmodic musculoskeletal movements. These conditions increasingly incapacitate the patient over time, if left untreated.

These disorders are often treated using medications. The medications do not always work as desired. Other types of treatment are also present. One type of treatment is deep brain stimulation (DBS), which can provide relief and restore a great degree of motor function.

Deep brain stimulation uses a medical device called a neurostimulator, which sends electrical impulses through implanted electrodes to specific targets in the brain for the treatment of movement and neuropsychiatric disorders. These electrodes transmit low-level electrical pulses that effectively buffer and normalize neurological misfiring in the brain.

Deep brain stimulation in select brain regions has provided therapeutic benefits for otherwise treatment-resistant disorders. Deep brain stimulation directly changes brain activity in a controlled manner.

Although deep brain stimulation may be effective in treating these disorders, the underlying principles and mechanisms are still not clear. The pulse generator may be programmed by sending electrical signals through electrodes in the brain that have a selected pulse width, voltage amplitude, and frequency. Adjustments to these parameters may be made to obtain desired results in a patient, such as a reduction in tremors.

As high tech as this technology is, it has been in use since the 1930's, and the standard interface used today in programming neurostimulators for deep brain stimulation is at least 15 years old, cumbersome, awkward, and requires undue cognitive overhead for an operator, such as a doctor or technician, to translate 3-dimensional anatomical positions into a series of numbers.

Therefore, it would be desirable to have a method and apparatus that take into account at least some of the issues discussed above, as well as other possible issues. For example, it would be desirable to have a method and apparatus that overcome a technical problem with managing medical device systems, and in particular, to more effectively making adjustments to the operation of a neurostimulator for deep brain stimulation.

SUMMARY

An aspect of the present disclosure provides a visualization system for deep brain stimulation. The visualization system comprises a camera system, a display system, and an information analyzer. The information analyzer is configured to communicate with the camera system and the display system. The information analyzer is configured to display a group of electrodes for the deep brain stimulation on a head of a patient on the display system such that a visualization of the group of electrodes is displayed overlaid on the head of the patient in real time in a position corresponding to an actual position of the group of electrodes in a brain in the head of the patient. An operation of the group of electrodes sending an electrical signal into the head of the patient is displayed in the visualization, enabling visualizing a physical reaction of the patient to the deep brain stimulation in conjunction with the visualization of the operation of the group of electrodes.

Another aspect of the present disclosure provides a method for visualizing deep brain stimulation. The method comprises receiving stimulation information about an operation of a group of electrodes in a brain of a patient for the deep brain stimulation. The stimulation information is received in real time during the operation of the group of electrodes. The method displays the group of electrodes on a head of the patient on a display system such that a visualization of the group of electrodes is displayed overlaid on the head of the patient in real time in a position corresponding to an actual position of the group of electrodes in the brain in the head of the patient. The method displays the visualization of the operation of the group of electrodes sending an electrical signal into the head of the patient, enabling a view of a physical reaction of the patient to the deep brain stimulation in conjunction with the visualization of the operation of the group of electrodes.

Yet another aspect of the present disclosure provides a visualization system for a medical device system. The visualization system comprises a camera system, a display system, and an information analyzer. The information analyzer is in communication with the camera system and the display system. The information analyzer is configured to display the medical device system on a body of a patient on the display system such that a visualization of the medical device system is displayed overlaid on the body of patient with the visualization in real time in a position corresponding to an actual position of the medical device system and an operation of the medical device system is displayed in real time.

The features and functions can be achieved independently in various examples of the present disclosure or may be combined in yet other examples in which further details can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and features thereof, will best be understood by reference to the following detailed description of an illustrative example of the present disclosure when read in conjunction with the accompanying drawings, wherein:

DETAILED DESCRIPTION

The illustrative examples recognize and take into account one or more different considerations. For example, the illustrative examples recognize and take into account that current techniques for programming a neurostimulator using a data processing system, such as a computer, a tablet, a mobile phone, or some other device that can use wired or wireless connections. The illustrative examples recognize and take into account that the interface currently provided through the data processing system enables an operator to enter values to control parameters of electrical signals that are generated by the neurostimulator and emitted through the electrodes. The current interface used by an operator to see information and program the neurostimulator is extremely complex and receives user input in the form of alphanumeric data. The operator may be a doctor, a technician, a nurse, or other person that can monitor and adjust the operation of the neurostimulator.

Further, the illustrative examples recognize and take into account that this interface does not provide the operator any feedback as to the results of changes in the electrical signals generated by the neurostimulator. The illustrative examples recognize and take account that the operator is currently required to observe the patient in which the deep brain stimulation system is implanted and analyze the electrical signals being generated to determine if changes may be needed to obtain desired results using an interface on a data processing system, such as a handheld device.

For example, the illustrative examples recognize and take into account that an operator, such as a doctor, observes as the patient performs a battery of motor function tests while making adjustments, via the interface on the hand-held device, to program the neurostimulator. The illustrative examples recognize and take account that the doctor simultaneously watches the patient, the patient's vitals, the patient's response, directs actions for the patient to take, inquires about sensations perceived by the patient, imagines the location of embedded electrodes in the brain, imagines which station along the electrode is being activated, imagines how much current is being administered, considers which brain structures are being affected from the electrical pulse, watches the hand held device to keep in mind what impulses are being administered to which electrodes and at which electrode stations, considers all interactions that can occur from the multiple impulses being given at each location, as well taking into account as other factors. These examples recognize and take into account that these actions require large amounts of concentration and focus by the doctor.

The illustrative examples recognize and take account that would be useful to have an improved user interface allowing an operator to more easily program a neurostimulator. Thus, the illustrative examples provide a method and apparatus for visualizing deep brain stimulation. In one illustrative example, stimulation information about an operation of a group of electrodes in the brain of a patient for deep brain stimulation is received. The stimulation information is received in real time during operation of the group of electrodes. The process displays the group of electrodes on a head of a patient on the display system such that the group of electrodes is displayed overlaid on a view of the head of the patient in real time in a position corresponding to the actual position of the group of electrodes in a brain in the head of the patient. The process also displays a visualization of an operation of the group of electrodes sending an electrical signal into the head of the patient.

This visualization enables a view of a physical reaction of the patient to the deep brain stimulation, in conjunction with the visualization of the operation of the group of electrodes. For example, the visualization of the signals being generated are displayed in a manner that augments the view of the patient seen by the operator. In this manner, the operator may visualize the generation of electoral signals and how those signals change or reduce physical manifestations of a disorder being treated using the brain stimulation. This type of visualization aids an operator in focusing on the task of analyzing, and potentially modifying, the operation of a neurostimulator more easily as compared to currently used techniques.

Figure 1:
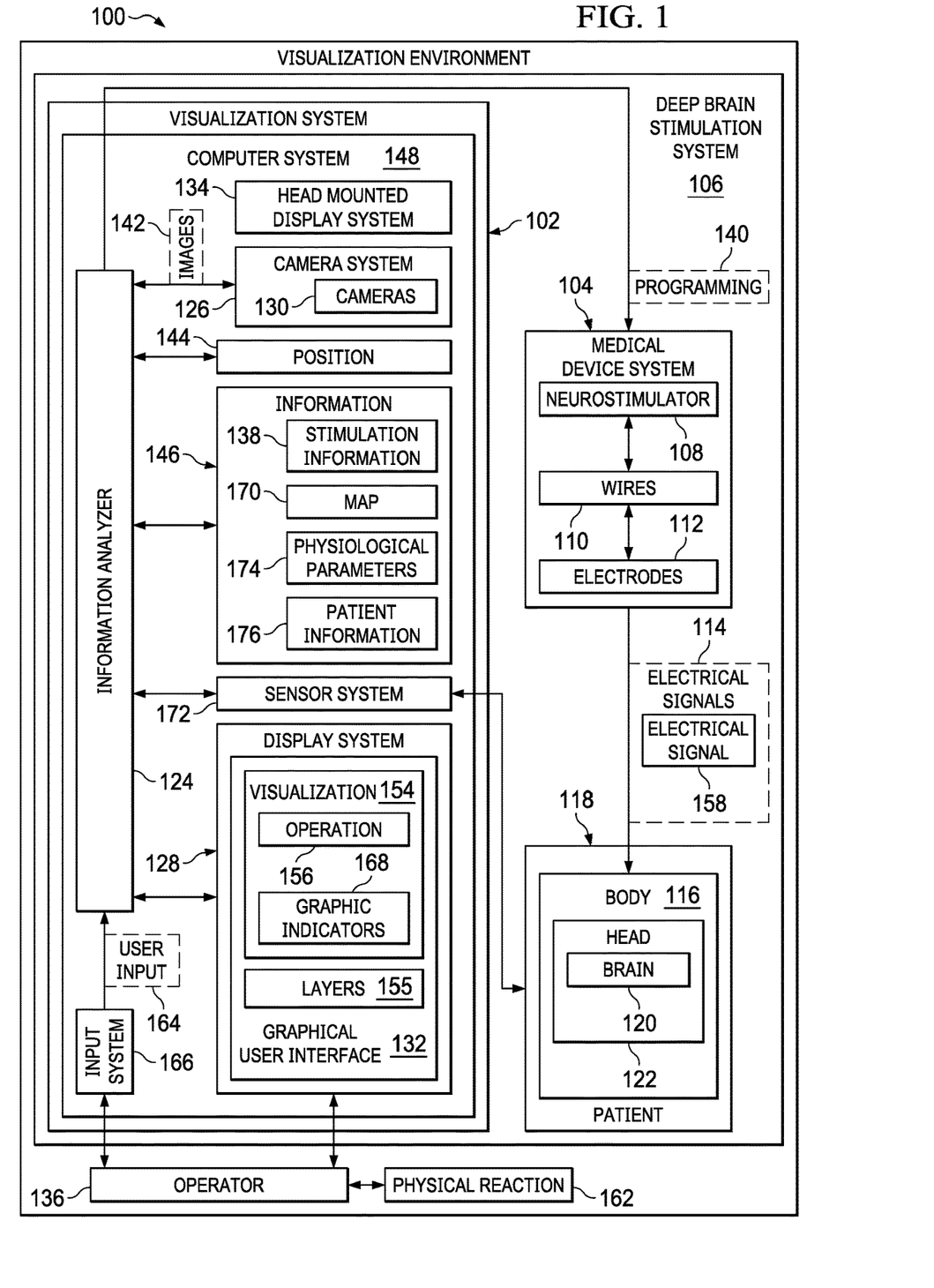
FIG. 1 is an illustration of a block diagram of a visualization environment for medical devices in accordance with an illustrative example.

With reference now to the figures, and in particular, with reference to FIG. 1, an illustration of a block diagram of a visualization environment for medical devices is depicted in accordance with an illustrative example. As depicted, visualization environment 100 includes visualization system 102. In this illustrative example, visualization system 102 is utilized to manage the operation of medical device system 104, which takes the form of deep brain stimulation system 106, in this particular example.

As depicted, deep brain stimulation system 106 comprises a number of different components. As illustrated in this example, deep brain stimulation system 106 comprises neurostimulator 108, wires 110, and electrodes 112.

Neurostimulator 108 is a device that generates electrical signals 114. Neurostimulator 108 may be implanted in body 116 of patient 118. Patient 118 is a person in which neurostimulator 108 is implanted. Patient 118 could also be an animal in other illustrative examples. Electrodes 112 are implanted in brain 120 in head 122 of patient 118. Wires 110 connect neurostimulator 108 and electrodes 112 to each other. Wires 110 also may be located within body 116 of patient 118.

Neurostimulator 108 generates electrical signals 114 that may travel to electrodes 112 through wires 110. Electrodes 112 emits electrical signals 114 into brain 120 in head 122 during operation of neurostimulator 108.

In this illustrative example, visualization system 102 includes a number of different components. As depicted, visualization system 102 comprises information analyzer 124, camera system 126, and display system 128.

As depicted, camera system 126 is comprised of a group of cameras 130. As used herein, "a group of" when used with reference to items means one or more items. For example, a group of cameras 130 is one or more of cameras 130. Camera system 126 can generate images 142 for a video to provide a live view of patient 118.

Display system 128 is a physical hardware system and includes one or more display devices on which graphical user interface 132 may be displayed. The display devices can include at least one of a light emitting diode (LED) display, a liquid crystal display (LCD), an organic light emitting diode (OLED) display, or some other suitable device on which graphical user interface 132 can be displayed.

As used herein, the phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A, one of item B, and ten of item C; four of item B and seven of item C; or other suitable combinations.

The components in visualization system 102 can be implemented in a number different ways. For example, these components can be located in computer system 148. Computer system 148 is a physical hardware system and includes one or more data processing systems. When more than one data processing system is present, those data processing systems are in communication with each other using a communications medium. The communications medium may be a network. The data processing systems can be selected from at least one of head mounted display system, a computer, a server computer, a tablet, or some other suitable data processing system.

As depicted, computer system 148 can take the form of or include head mounted display (HMD) system 134 in which these components are integrated in head mounted display system 134. Head mounted display system 134 may take a number of different forms. For example, head mounted display system 134 can be selected from a group comprising smart glasses, hololens, or some other type of display system that may be worn on the head of operator 136.

In one illustrative example, display system 128 and camera system 126 are located in head mounted display system 134. Information analyzer 124 is located in at least one of a head mounted display system or a remote data processing system in computer system 148.

In this illustrative example, operator 136 is a person. Operator 136 can be a doctor, a technician, or some other person that utilizes visualization system 102.

As depicted, information analyzer 124 in visualization system 102 is configured to communicate with camera system 126, display system 128, and neurostimulator 108 in deep brain stimulation system 106. As depicted, the communication with these components are performed using a physical or wireless communications link. A physical communications link can be established using at least one of a wire cable, an optical cable, or some other physical medium that may allow for an exchange of information between information analyzer 124 in visualization system 102 and at least one of camera system 126, display system 128, and neurostimulator 108. Wireless communication can be performed using a wireless link that employs at least one of radiofrequency signals, magnetic signals, or some other type of wireless signal.

Information analyzer 124 is configured to receive stimulation information 138 from neurostimulator 108 regarding the operation of neurostimulator 108. Information analyzer 124 is configured to receive stimulation information 138 about operation 156 of the group of electrodes 112 in brain 120 of patient 118 for deep brain stimulation. As depicted, stimulation information 138 is received in real time during operation 156 of the group of electrodes 112.

Stimulation information 138 is an example of information 146 and can include operational parameters, information about electrical signals 114 generated by neurostimulator 108, and other suitable types of data.

As depicted in this illustrative example, information analyzer 124 transmits programming 140 from information analyzer 124 to neurostimulator 108. Programming 140 can include commands, program code, parameters, or other information that may be used to access stimulation information 138, control, or modify the operation of neurostimulator 108.

Information analyzer 124 also can receive images 142 from camera system 126. Images 142 can be used by information analyzer 124 to identify position 144 of head 122 or other portions of body 116 of patient 118. In this illustrative example, position 144 includes the location in three-dimensional space. Further, position 144 also includes identification of the orientation of head 122 or other portions of body 116.

In this illustrative example, position 144 can be used to determine where to display information 146 in association with patient 118 from the view of camera system 126 in visualization 154.

In the illustrative example, information 146 is any information relating to patient 118, which includes information about medical device system 104. For example, information 146 includes at least one of stimulation information 138, patient information 176, or other suitable information related to patient 118. Information 146 can be displayed in layers 155 in graphical user interface 132 as part of visualization 154. Each of these types of information 146 can be displayed as a layer in layers 155 for visualization 154 in graphical user interface 132. In this illustrative example, patient information 176 about patient 118 includes at least one of an image, a patient record, an x-ray, a computer aided tomography (CAT) scan, a thermal map, a magnetic resonance imaging (MRI) scan, or some other type of information.

The use of layers 155 can allow for easier manipulation of at least one of different types of information 146 or different pieces of the same type of information 146 displayed in graphical user interface 132. For example, different ones of layers 155 can be selected for display in visualization 154 in graphical user interface 132. By using layers 155, at least one of different types of information 146 or different pieces of the same type of information 146 can be displayed, removed, moved, or otherwise manipulated in visualization 154 displayed in graphical user interface 132. The manipulation of the types of information 146 can be performed at the same time, in a particular order, or both.

Information 146 is displayed in layers 155 in association with the view of patient 118 by being displayed on body 116 of patient 118 or in a location proximate to body 116 in visualization 154 in a manner that information 146 is considered to be for patient 118. Each layer in layers 155 displayed in visualization 154 in graphical user interface 132 may be manipulated independently of another layer in layers 155.

Images 142 also can be displayed in graphical user interface 132 as part of visualization 154. For example, images 142 can be utilized to provide a live view of patient 118. Images 142 also can be displayed in layers 155.

During operation of visualization system 102, information analyzer 124 is in communication with camera system 126 and display system 128. Information analyzer 124 also communicates with neurostimulator 108.

As depicted, information analyzer 124 is configured to display a group of electrodes 112 for a deep brain stimulation on head 122 of patient 118 on display system 128 such that visualization 154 of the group of electrodes 112 is displayed overlaid on head 122 of patient 118 in graphical user interface 132 in real time in position corresponding to the actual position of the group of electrodes 112 in brain 120 in head 122 of patient 118. The display of the group of electrodes 112 is also made within a layer in layers 155. The display in a layer allows for the display of the group of electrodes 112 to be manipulated separate from other items in other layers. For example, the group of electrodes 112 may be manipulated to control the manner in which signals are emitted by the group of electrodes 112.

Information analyzer 124 is also configured to display operation 156 of the group of electrodes 112 sending electrical signal 158 into head 122 of patient 118 is displayed in real time. As depicted visualization 154 of operation 156 of the group of electrodes 112 comprises information analyzer 124 displaying graphic indicators 168 in graphical user interface 132 on display system 128 indicating at least one of a current flow or a voltage from the group of electrodes 112 into brain 120.

A graphic indicator in the group of graphic indicators can be selected from at least one of an icon, an image, an animation, or some other suitable graphic to indicate a flow of current, voltage, or both into the brain of a patient. In this manner, the group of graphical indicators 168 allow the group of electrodes 112 to be visualized. For example, information relating to the operation of the group of electrodes 112 can be visualized by lighting up individual electrodes with different colors. The signals emitted by the individual electrodes can be represented by size, shape, amplitude, and pulse rate, current flow, and other information that can be displayed visually through changes in color, flat-rate, element size, pattern, correction of a moving pattern, and other types of graphical indicators 168 may be used.

In this manner, operator 136 is able to visualize physical reaction 162 of patient 118 to the deep brain stimulation using electrical signal 158 in conjunction with operation 156 of the group of electrodes 112 in visualization 154 generated by information analyzer 124. Electrical signal 158 is a selected from at least one of a continuous signal and a pulsed signal.

In this illustrative example, information analyzer 124 displays map 170 of brain 120 in a layer in layers 155 in graphical user interface 132 for visualization 154 of head 122 or on some other part of body 116 of patient 118. This display may be made during at least one of before, during, or after application of electrical signal 158. Map 170 of brain 120 is another example of information 146.

As depicted, map 170 of brain 120 in visualization 154 in graphical user interface 132 may include regions selected from at least one of a hindbrain, a midbrain, a forebrain, a cerebral hemisphere, a cerebral lobe, a frontal lobe, a temporal lobe, an occipital lobe, a parietal lobe, a cerebral cortex, or some other region in the brain. As another example, map 170 of brain 120 displayed in graphical user interface 132 for visualization 154 may be a map of regions identified by functions selected from at least one of hearing, sight, emotion, speech, pain, hunger, smell, or some other suitable function.

Map 170 may be generated any number different ways. For example, map 170 may be generated from at least one of a computer tomography (CT) scan, a computerized axial tomography (CAT) scan, a positron-emission tomography (PET) scan, a magnetic resonance imaging (MRI) scan, an x-ray, or some other suitable imaging technique.

Visualization system 102 also can include sensor system 172. Sensor system 172 is utilized with patient 118 to detect a group of physiological parameters 174 for patient 118.

Physiological parameters 174 are parameters regarding the function of body 116. In this example, a group of physiological parameters 174 comprises at least one of a heart rate, a body temperature, a galvanic skin response, a blood pressure, a sugar level, a respiratory rate, a respiratory volume, or some other suitable parameter.

The group of physiological parameters 174 is another example of information 146. With the detection of the group of physiological parameters 174, additional information may be visualized in visualization 154 displayed in graphical user interface 132. The group of physiological parameters 174 can be displayed in one or more of layers 155 in visualization 154 in graphical user interface 132.

For example, information analyzer 124 can be configured to display the group of physiological parameters 174 in a layer in layers 155 as part of visualization 154 of head 122 of patient 118 in graphical user interface 132 on display system 128.

As depicted, information analyzer 124 can display patient information 176 about patient 118 in association with the view of patient 118 on display system 128 as part of visualization 154. In this manner, visualization 154 of information 146 overlaid on or near head 122 of patient 118 provides an augmented reality visualization. This information can be displayed by identifying patient 118.

Further, operator 136 can interact with graphical user interface 132 through user input 164 generated by input system 166 for computer system 148. Input system 166 is a physical hardware system and may be selected from at least one of a mouse, a keyboard, a trackball, a touchscreen, a stylus, a motion sensing input device, a cyber glove, or some other suitable type of input device.

For example, operator 136 can use gestures to select one or more of electrodes 112 and manipulate the operation of electrodes 112. As depicted, input system 166 can detect gestures made by operator 136 to generate user input 164. As depicted, operator 136 may use gestures to change parameters about the generation of electrical signals 114. For example, the size or extent to which electrical signals 114 travel into brain 120 can be changed in size through gestures made by operator 136. For example, parameters, such as the magnitude of the current, the magnitude of the voltage, the distance the current travels, the distance the voltage travels, or some other premature about the effects of electrical signals 114 in brain 120 may be visualized. These gestures made by operator 136 can change, for example, a voltage, a current, a pulse width, a frequency, or some other parameter relating to electrical signals 114.

Additionally, operator 136 also may use gestures to select information 146 for display in visualization 154 in graphical user interface 132. For example, gestures can be made by operator 136 to display desired pieces of patient information 176. The display of information 146 can be managed by operator 136 manipulating layers 155 displaying information 146 in visualization 154 in graphical user interface 132.

In the illustrative example, information analyzer 124 can be implemented in software, hardware, firmware or a combination thereof. When software is used, the operations performed by information analyzer 124 can be implemented in program code configured to run on hardware, such as a processor unit. When firmware is used, the operations performed by information analyzer 124 can be implemented in program code and data and stored in persistent memory to run on a processor unit. When hardware is employed, the hardware may include circuits that operate to perform the operations in information analyzer 124.

In the illustrative examples, the hardware can take a form selected from at least one of a circuit system, an integrated circuit, an application specific integrated circuit (ASIC), a programmable logic device, or some other suitable type of hardware configured to perform a number of operations. With a programmable logic device, the device may be configured to perform the number of operations. The device can be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes can be implemented in organic components integrated with inorganic components and may be comprised entirely of organic components, excluding a human being. For example, the processes can be implemented as circuits in organic semiconductors.

One or more examples are present that overcome issues with managing medical device systems, and in particular, to more effectively making adjustments to the operation of a neurostimulator for deep brain stimulation. As a result, a simultaneous visualization of a patient and patient information in real time is provided in a manner that enables an operator, such as a doctor or technician, to manage the operation of a medical device system, such as deep brain stimulation, more easily through a graphical user interface that displays an augmented reality view of the medical device system with a patient in which the medical device system is implanted.

As a result, computer system 148 operates as a special purpose computer system in which information analyzer 124 in computer system 148 enables visualizing the operation of medical device system 104, and in particular, deep brain stimulation system 106. In particular, information analyzer 124 transforms computer system 148 into a special purpose computer system as compared to currently available general computer systems that do not have information analyzer 124.

For example, information analyzer 124 displays graphical user interface 132 in a manner to provide visualization 154 of the operation of deep brain stimulation system 106 within head 122 of patient 118. In this manner, graphical user interface 132 is a visual tool provided through information analyzer 124 in computer system 148 to operator 136 in managing deep brain stimulation system 106. Visualization 154 in graphical user interface 132 can be provided through program code, hardware, or some combination thereof in information analyzer 124 that configures information analyzer 124 to display graphical user interface 132 on display system 128.

The illustration of visualization environment 100 in FIG. 1 is not meant to imply physical or architectural limitations to the manner in which an illustrative example may be implemented. Other components, in addition to or in place of the ones illustrated, may be used. Some components may be unnecessary. Also, the blocks are presented to illustrate some functional components. One or more of these blocks may be combined, divided, or combined and divided into different blocks when implemented in an illustrative example.

For example, although display system 128 is described as a component of head mounted display system 134, display system 128 can take other forms. For example, display system 128 can be selected from at least one of a display for a tablet display system, a touch screen, pico projector, a holographic projector, or some other suitable type of display system that projects light onto a surface, such as that on head 122 or some other portion of body 116 of patient 118. With a pico projector or a holographic projector, graphical user interface 132 can be displayed directly on head 122 of patient 118. For example, graphical user interface 132 provides visualization 154 by displaying electrodes 112 on head 122 of patient 118. Further, operation 156 of electrodes 112 can be visualized using graphic indicators 168. The display system can be a wireless contact lens display in which images and information may be displayed using light projected through the center of the pupil working with optics in the eye to focus the display on the retina in the art. As a result, two separate images can be superimposed on the retina to create one integrated image for an augmented reality visualization.

Other types of user input can be used, in addition to or in place of gestures, to generate user input 164 by input system 166. For example, user input 164 can be generated through gaze, voice, or other types of input, in addition to or in place of gestures. Video, audio, or other information also can be part of information 146 that is displayed in visualization 154 in graphical user interface 132.

As another example, medical device system 104 may take other forms for purposes other than for deep brain stimulation. For example, the generation of electrical signals 114 may be initiated through medical device system 104 in the form of a pacemaker, a defibrillator, or some other suitable type of device that generates electrical signals 114 within body 116. In this manner, the visualization of the manner in which other medical devices generating electrical signals 114 also may be visualized by an operator for use in managing medical device system 104. As another example, medical device system 104 may be a memory, an image processor, or some of suitable device that may be implemented within body 116 that generates electrical signals 114. As yet another illustrative example, medical device system 104 may generate electrical signals 114 to stimulate muscle contraction.

Figure 2:
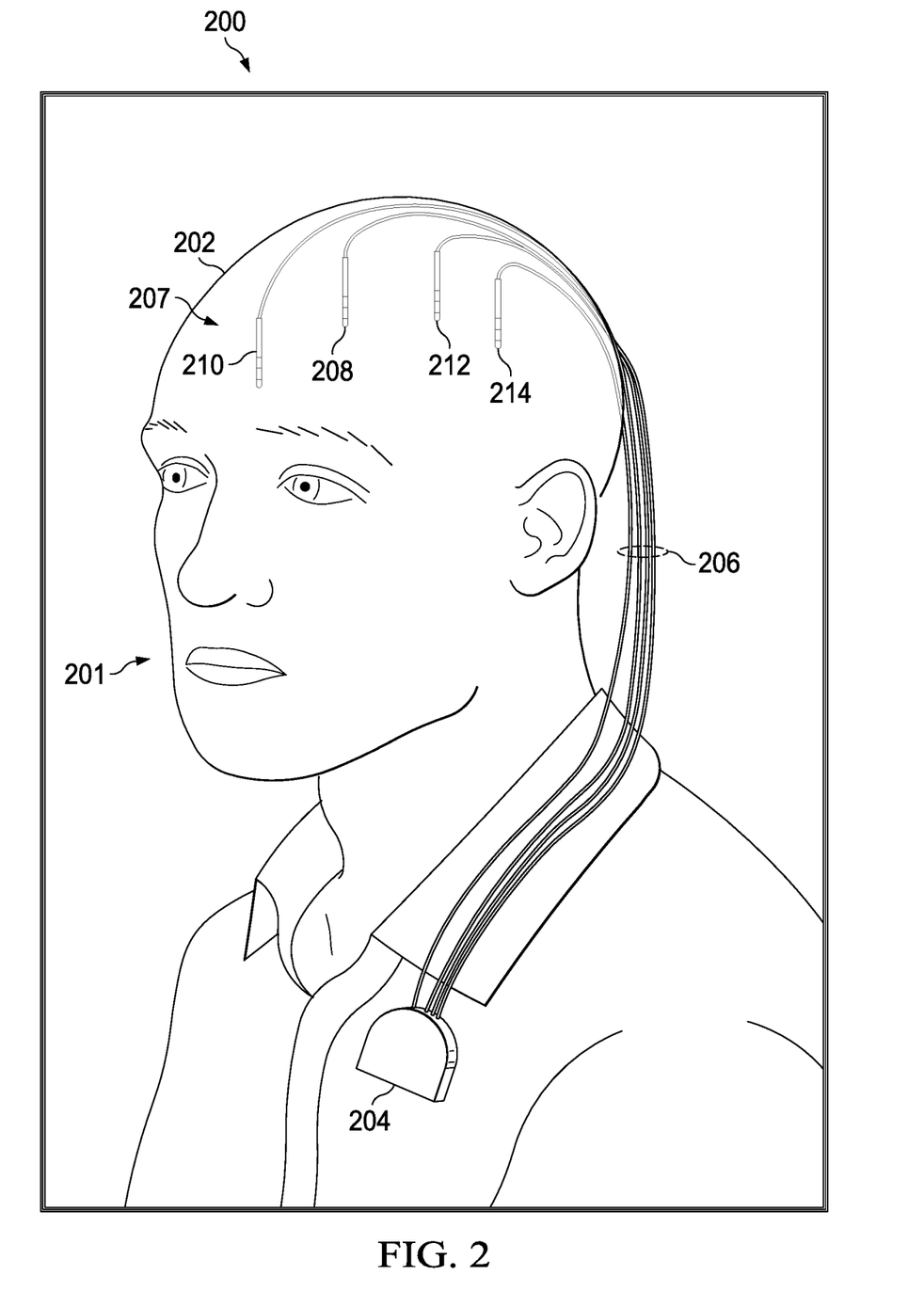
FIG. 2 is an illustration of a graphical user interface used to provide a visualization in the form of augmented reality visualization in accordance with an illustrative example.

With reference next to FIG. 2, an illustration of a graphical user interface used to provide a visualization in the form of an augmented reality visualization is depicted in accordance with an illustrative example. In this illustrative example, graphical user interface 200 is an example of one implementation for graphical user interface 132 shown in block form in FIG. 1 that is displayed on display system 128 in visualization system 102 to provide an augmented reality visualization.

Patient 202 may be displayed in graphical user interface 200 from images generated of patient 202. In other illustrative examples, patient 202 in graphical user interface 200 may be seen through lenses or other optical elements in a visualization system in which graphical user interface 200 is displayed to provide an augmented reality visualization. In these examples, a live view of patient 202 is presented in the visualization system.

In this illustrative example, graphical user interface 200 shows deep brain stimulation system 201. These components include neurostimulator 204, wires 206, and electrodes 207. As shown in this particular example, electrodes 207 include electrode 208, electrode 210, electrode 212, and electrode 214. The display of electrodes 207 may be within a layer that is displayed within graphical user interface 200.

As depicted, neurostimulator 204 is shown in graphical user interface 200 as an actual component in a live view of patient 202. Wires 206 and electrodes 207 are implanted inside of patient 202 and are shown using graphical indicators. The different components are shown in the locations where the components are actually located in patient 202. The location includes a position identified using three-dimensional components and an orientation of the components.

In this illustrative example, graphical user interface 200 provides an augmented reality visualization in a manner that allows for more efficient analysis of the operation of deep brain stimulation system 201. By overlaying the components in deep brain stimulation system 201 onto patient 202, the visualization of these components and the location can aid in managing the operation of deep brain stimulation system 201.

Figure 3:
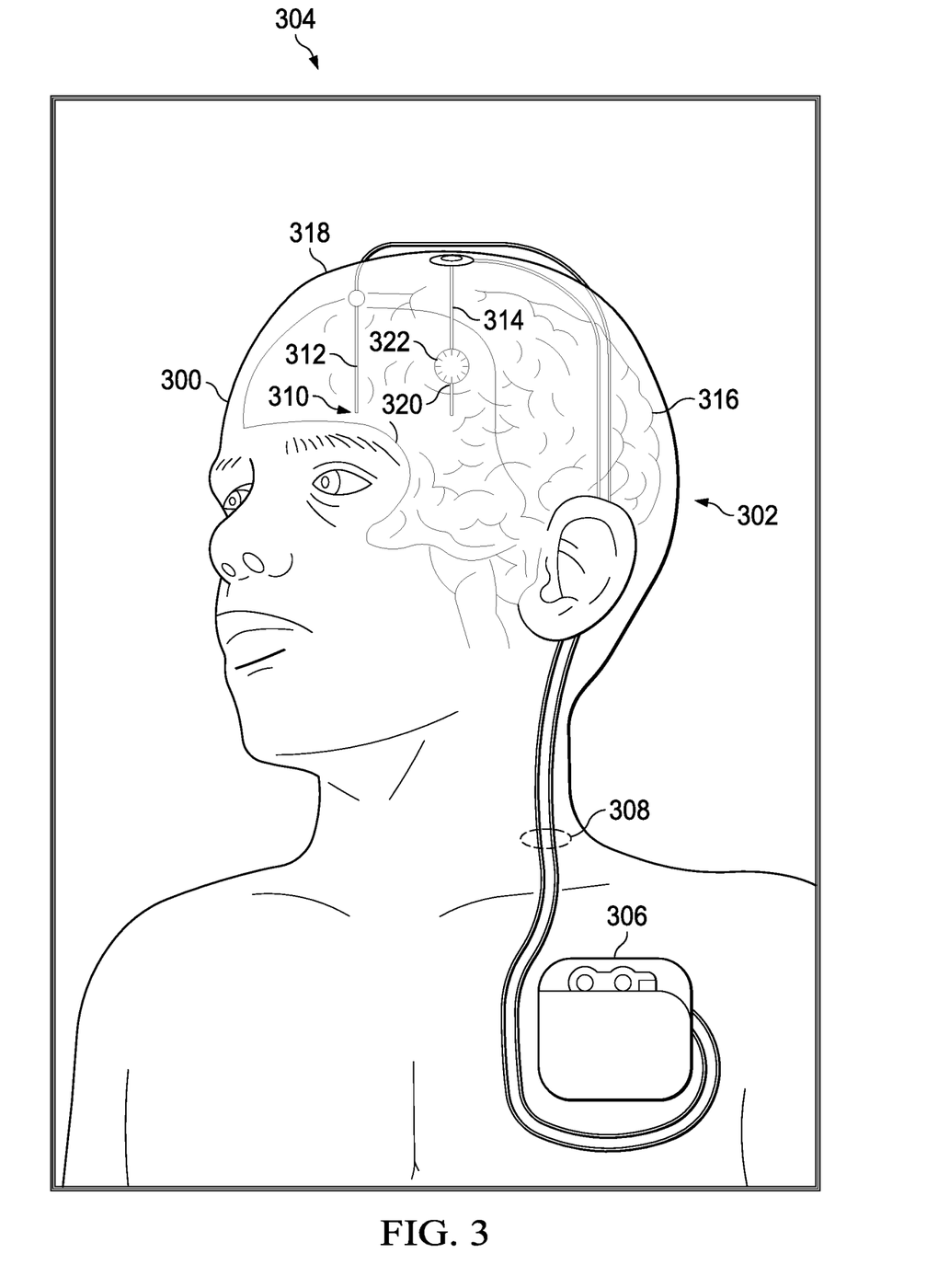
FIG. 3 is an illustration of a graphical user interface used to provide a visualization or an augmented reality visualization in accordance with an illustrative example.

With reference next to FIG. 3, an illustration of a graphical user interface used to provide a visualization in the form of an augmented reality visualization is depicted in accordance with an illustrative example. In this example, graphical user interface 304 is an example of one implementation for graphical user interface 132 shown in block form in FIG. 1 that is displayed on display system 128 in visualization system 102 to provide an augmented reality visualization.

In this illustrative example, a live view of patient 300 is shown with deep brain stimulation system 302 in graphical user interface 304. As depicted, deep brain stimulation system 302 includes neurostimulator 306, wires 308, and electrodes 310. Electrodes 310 comprise electrode 312 and electrode 314. In this illustrative example, these different components of deep brain stimulation system 302 are displayed using graphical indicators overlaid on a live view of patient 300 to provide an augmented reality visualization. The different components in deep brain stimulation system 302 can be displayed in a layer within graphical user interface 304.

In this depicted example, additional information is also displayed in graphical user interface 304. For example, brain 316 is displayed on head 318 of patient 300. The display of brain 316 along with deep brain stimulation system 302 provides additional information in the augmented reality visualization of deep brain stimulation system 302. In this example, the display of brain 316 can be made using a different layer from the display of components in deep brain stimulation system 302.

Additionally, graphical indicator 320 displayed in graphical user interface 304 and represents a voltage signal. The display voltage signal using graphical indicator 320 provides a visualization of the operation of deep brain stimulation system 302. This display can indicate the station on electrode 314 in electrodes 310. The station indicates where along the electrode 314 voltage signal 322 propagates from electrode 314. This type of information provides an augmented reality view that is more intuitive and efficient for programming or quantifying the program of deep brain stimulation system 302.

Figure 4:
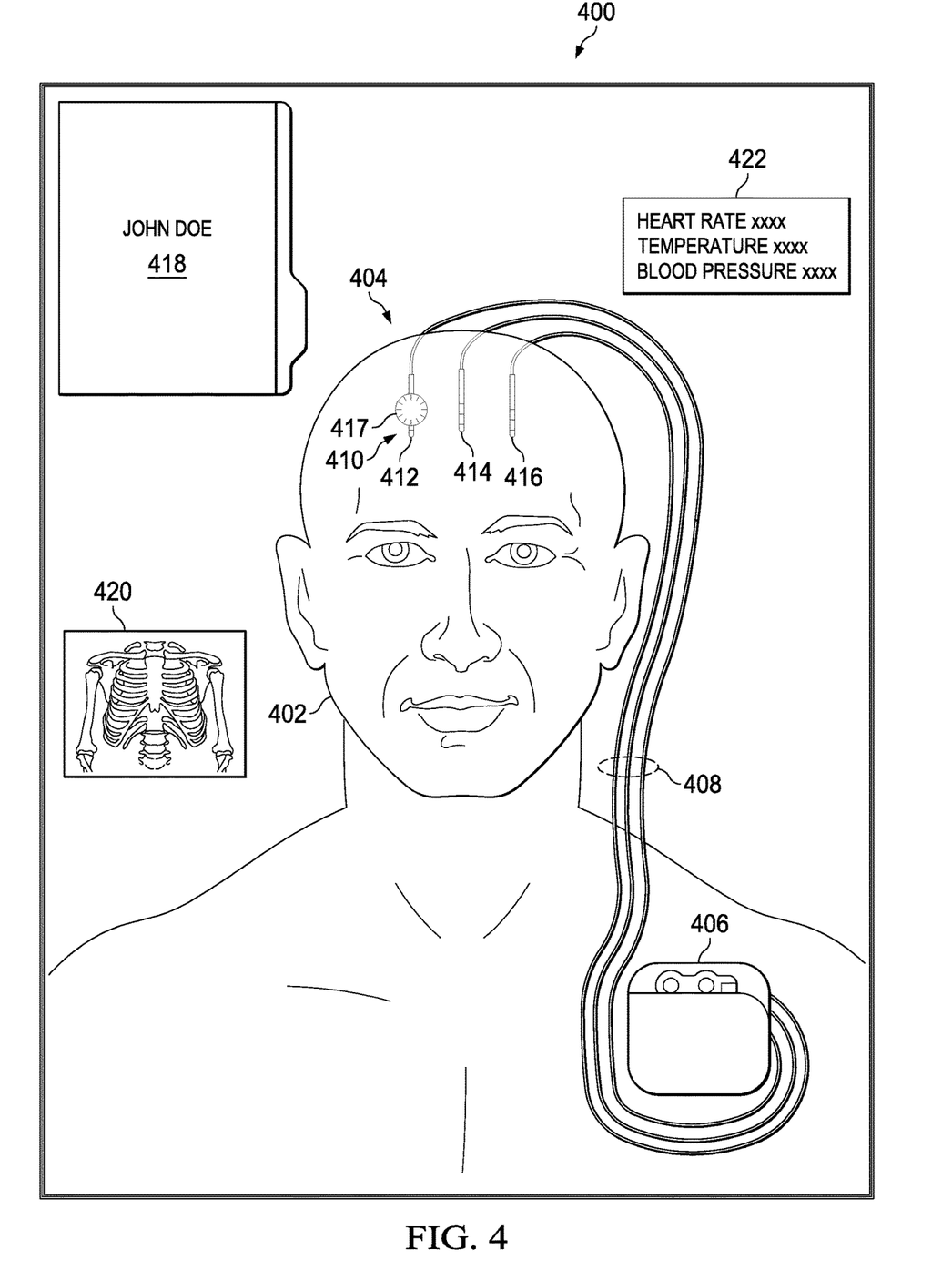
FIG. 4 is an illustration of a graphical user interface used to provide a visualization in the form of an augmented reality visualization in accordance with an illustrative example.

With reference next to FIG. 4, an illustration of a graphical user interface used to provide a visualization in the form of an augmented reality visualization is depicted in accordance with an illustrative example. In this illustrative example, graphical user interface 400 is an example of one implementation for graphical user interface 132 shown in block form in FIG. 1 that is displayed on display system 128 in visualization system 102 to provide an augmented reality visualization. In this illustrative example, a live view of patient 402 is displayed in graphical user interface 400.

In this illustrative example, graphical user interface 400 depicts deep brain stimulation system 404. These components include neurostimulator 406, wires 408, and electrodes 410. As shown in this particular example, electrodes 410 include electrode 412, electrode 414, and electrode 416. The display of electrodes 410 can be within a layer that is displayed within graphical user interface 400.

As depicted, voltage signal 417 is displayed as being emitted from electrode 412. The display of voltage signal 417 can be performed as an animation to show the extent to which voltage signal 417 travels within patient 402. Animation can be used to also show the frequency, duration, and other parameters of voltage signal 417.

Further, patient information 418 is displayed in graphical user interface 400. In this illustrative example, patient information 418 is displayed as an icon indicating that information about patient 402 is available for viewing within graphical user interface 400. In other words, patient information 418 can be selected to obtain more detailed information about patient 402. As depicted, X-ray 420 is also displayed in graphical user interface 400.

Physiological parameters 422 are also displayed in graphical user interface 400. These parameters are shown in real time as a sensor system detects the parameters.

As depicted in this particular example, all information is displayed on a live view of patient 402. The different types of information can be displayed in layers in these illustrative examples.

In this manner, a human operator may more easily visualize information about patient 402 to determine whether adjustments are needed and what adjustments should be made to the operation of deep brain stimulation system 404.

Figure 5:
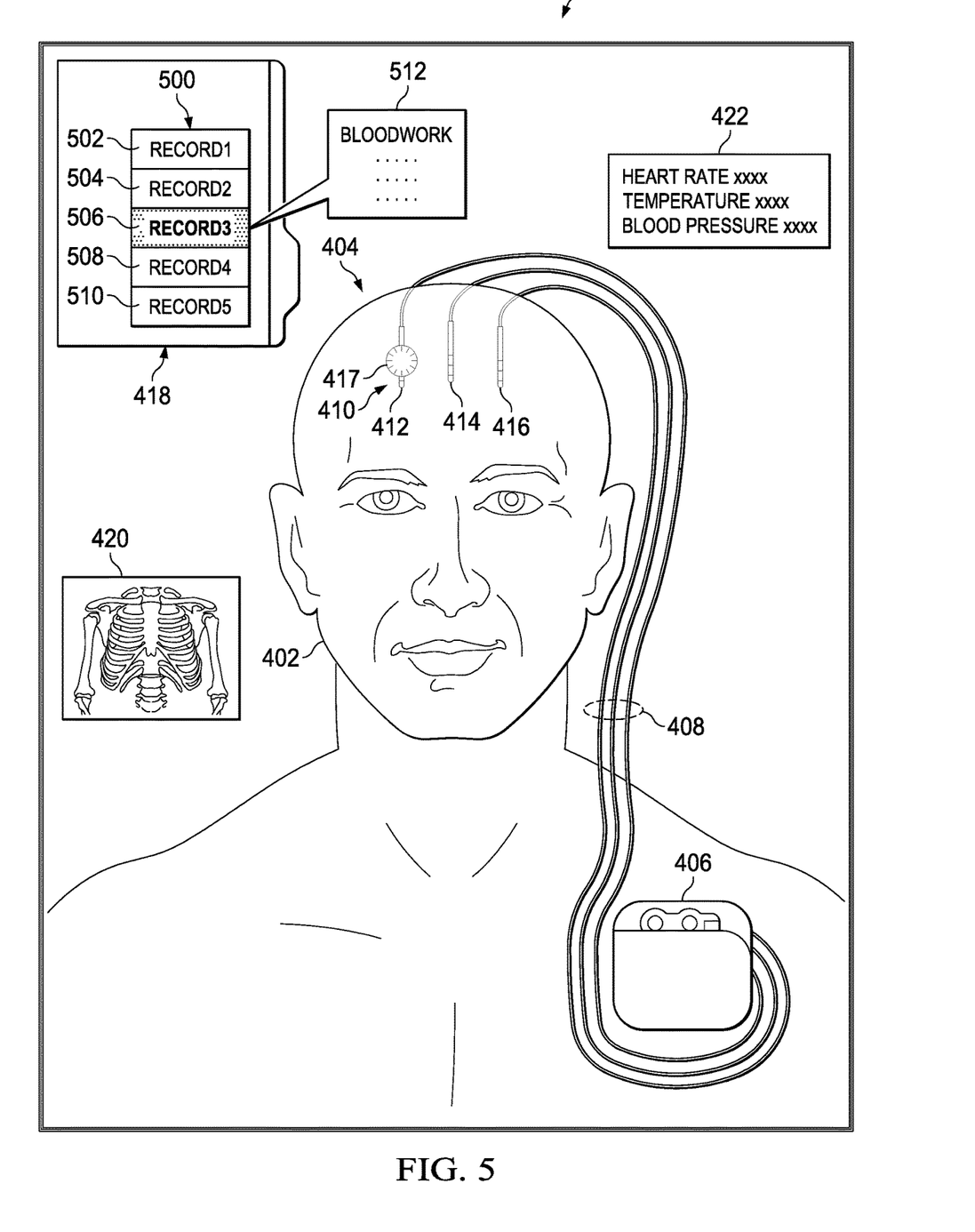
FIG. 5 is an illustration of a graphical user interface used to provide a visualization in the form of an augmented reality visualization in accordance with an illustrative example.

With reference now to FIG. 5, an illustration of a graphical user interface used to provide a visualization in the form of an augmented reality visualization is depicted in accordance with an illustrative example. In this figure, user input has been applied to graphical user interface 400 as shown in FIG. 4.

In this example, patient information 418 has been selected through user input. As a result, menu 500 is displayed. Menu 500 shows five records, record 502, record 504, record 506, record 508, record 510, which are present for patient 402. User input may be employed to select different records from patient information 418.

In this illustrative example, record 506 has been selected through user input. The selection of record 506 results in pop-up window 512 being displayed in graphical user interface 400. Pop-up window 512 shows bloodwork for patient 402.

In this manner, the operator viewing graphical user interface 400 may view the bloodwork for patient 402 while seeing other information for patient 402 all within the same view. In this manner, looking at different screens, closing and opening files, and other operations that may distract or require additional concentration can be avoided. As a result, the human operator can focus on viewing patient 402 and determining whether changes are needed to deep brain stimulation system 404.

The illustrations of graphical user interfaces in FIGS. 2-5 are provided as examples of some implementations for graphical user interface 132 shown in block form in FIG. 1. These examples not meant to limit the manner in which other illustrative examples can be implemented. For example, other illustrative examples can display other types of information in addition to or in place of information displayed in FIGS. 2-5. For example, other illustrative examples can provide for a live view of a torso of the patient in addition to the head of the patient.

In another illustrative example, graphical controls can be displayed in the graphical user interface for manipulation by an operator to change the operation of a deep brain stimulation system. The manner in which information is displayed in the different graphic user interfaces can be performed using techniques in addition to or in place of the ones illustrated in these figures. For example, instead of using pop-up window 512 in FIG. 5, a tooltip or other type of presentation mechanism can be used. Further, windows can be outlined or can be transparent such that only information is displayed.

Figure 6:
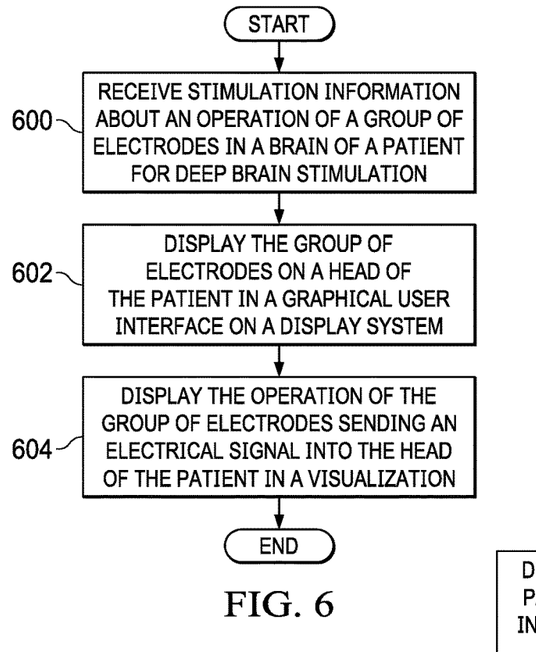
FIG. 6 is an illustration of a flowchart of a process for visualizing deep brain stimulation in accordance with an illustrative example.

Turning next to FIG. 6, an illustration of a flowchart of a process for visualizing deep brain stimulation is depicted in accordance with an illustrative example. The process depicted in FIG. 6 can be implemented in visualization environment 100 in FIG. 1. For example, the process can be implemented in information analyzer 124 within visualization system 102 to provide visualization 154 for the operation of medical device system 104.

In this example, as shown in FIG. 1, visualization 154 is provided through the display of graphical indicators 168 in graphical user interface 132. This visualization can include a live view of head 122 of patient 118 in which information 146 displayed using graphical indicators 168 augments the live view of head 122 to generate an augmented reality visualization. This visualization includes the operation of medical device system 104 and also can include information 146 regarding the effects of the operation of medical device system 104.

The process begins by receiving stimulation information about an operation of a group of electrodes in a brain of a patient for deep brain stimulation (operation 600). The stimulation information is received in real time during operation of the group of electrodes.

The process displays the group of electrodes on a head of a patient in a graphical user interface on a display system (operation 602). The display provides a visualization of the group of electrodes displayed overlaid on the head of the patient in the graphical user interface in real time. The group of electrodes is displayed in a position corresponding to an actual position of the group of electrodes in the brain in the head of the patient.

The process displays the operation of the group of electrodes sending an electrical signal into the head of the patient in a visualization (operation 604). The process terminates thereafter. In operation 604, displaying the operation of the group of electrodes comprises displaying a group of graphic indicators indicating at least one of a current flow or a voltage from the group of electrodes into the brain. Operation 604 enables a view of a physical reaction of the patient to the deep brain stimulation in conjunction with the visualization of the operation of the group of electrodes.

Figure 7:
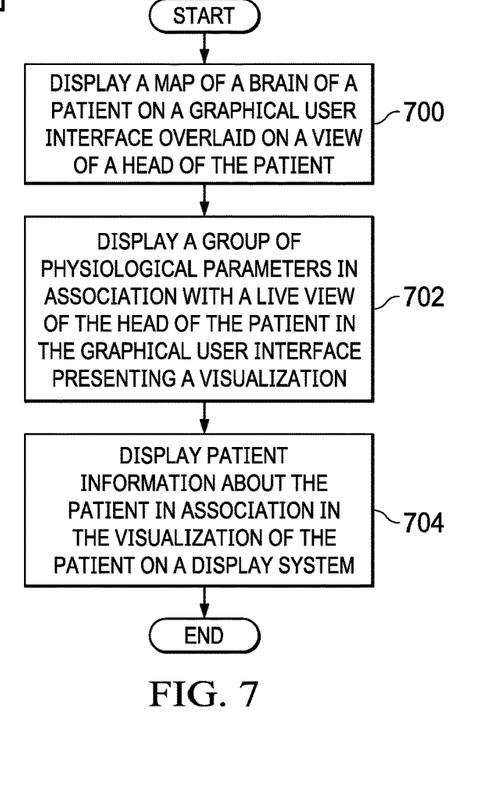
FIG. 7 is an illustration of a flowchart of a process for displaying information for a visualization of deep brain stimulation in accordance with an illustrative example.

With reference now to FIG. 7, an illustration of a flowchart of a process for displaying information for a visualization of deep brain stimulation is depicted in accordance with an illustrative example. The process in FIG. 7 may be performed in conjunction with the process in FIG. 1 to display information relating to the operation of the group of electrodes. This information may be obtained from a database, sensors, or other suitable sources.

The process begins by displaying a map of the brain of the patient on the graphical user interface overlaid on the view of the head of the patient (operation 700). In this manner, the view of the group of electrodes displayed in the process in FIG. 7, may be seen in conjunction with the regions of the brain in which the electrodes are located.

The process displays a group of physiological parameters in association with a live view of the head of the patient in the graphical user interface presenting visualization (operation 702). The process displays patient information about the patient in association in the visualization of the patient on the display system (operation 704). The process terminates thereafter. The information about the patient includes at least one of an image, a patient record, an x-ray, a computer aided tomography (CAT) scan, or a magnetic resonance imaging (MRI) scan.

The process in FIG. 7 may be repeated any number of times. For example, the displayed patient information can change as physiological parameters detected by sensor systems associated with the patient change.

Figure 8:
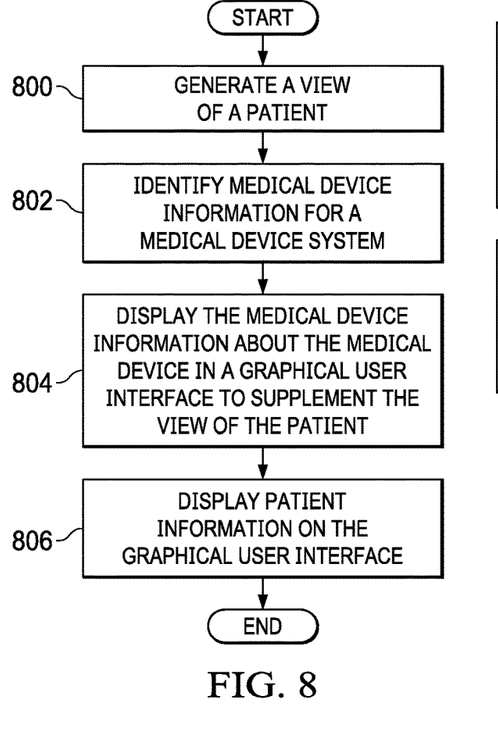
FIG. 8 is an illustration of a flowchart of a process for visualizing deep brain stimulation in accordance with an illustrative example.

Turning next to FIG. 8, an illustration of a flowchart of a process for visualizing deep brain stimulation is depicted in accordance with an illustrative example. The process depicted in FIG. 8 can be implemented in visualization environment 100 in FIG. 1. For example, the process may be implemented in information analyzer 124 within visualization system 102 to provide visualization 154 for the operation of medical device system 104. Medical device system 104 is any device that can be implanted in the human body performing physiological processes for to performing an action to obtain at least one of a pharmacological, immunological, or metabolic response.

In this example, medical device system 104 can take forms other than a deep brain stimulation system. For example, medical device system 104 may be a drug pump, a shunt, a pacemaker, a defibrillator, or some other suitable device.

The process begins by generating a view of a patient (operation 800). The view can be generated through images of the patient displayed in a graphical user interface or can be a view through lenses in a head mounted device.

The process identifies medical device information for the medical device system (operation 802). The medical device information includes information about the location of one or more components in the medical device system. Further, the medical device information also can include information regarding the operation of the medical device system. For example, electrical signals, magnetic signals, drugs, chemicals, or other items that may be injected into, propagated through, or introduced into the body of the patient as the medical device system operates are examples of medical device information. Other types of medical device information include parameters such as voltage, pulse width, timing, dosage, type of medication, and other suitable types of information relating to the medical device system.

The process displays medical device information about the medical device in the graphical user interface to supplement the view of the patient (operation 804). The supplementation provides an augmented reality visualization in this illustrative example. The medical device information can be a group of graphical indicators identifying the location of the medical device in the patient.

In this manner, the location, including three-dimensional position and orientation, of the medical device system in the patient can be seen through this visualization provided through the view of the patient with the medical device information. Additionally, the medical device information can include using a group of graphical indicators to provide a visualization of the operation of the medical device system. For example, electrical signals, magnetic signals, drugs, chemicals, or other items that can be injected into, propagated through, or introduced into the body the patient as the medical device system operates. This information is displayed in real time in this illustrative example.

The process also displays patient information on the graphical user interface (operation 806). The process terminates thereafter. This patient information can include information about the patient obtained from various records or database. The patient information also can be real-time information about physiological parameters measured using a sensor system associated with the patient.

With the visualization, an operator, such as a doctor, technician, or other person, can make adjustments to the operation of the medical device system. The visualization is provided through augmented reality visualization in which a view of the patient with the medical system in the operation of the system is seen. This visualization allows the operator to more easily focus on changes that can be needed in the operation of the medical device system.

The flowcharts and block diagrams in the different depicted examples illustrate the architecture, functionality, and operation of some possible implementations of apparatuses and methods in an illustrative example. In this regard, each block in the flowcharts or block diagrams can represent at least one of a module, a segment, a function, or a portion of an operation or step. For example, one or more of the blocks can be implemented as program code, hardware, or a combination of the program code and hardware. When implemented in hardware, the hardware can, for example, take the form of integrated circuits that are manufactured or configured to perform one or more operations in the flowcharts or block diagrams. When implemented as a combination of program code and hardware, the implementation can take the form of firmware. Each block in the flowcharts or the block diagrams can be implemented using special purpose hardware systems that perform the different operations or combinations of special purpose hardware and program code run by the special purpose hardware.

In some alternative implementations of an illustrative example, the function or functions noted in the blocks can occur out of the order noted in the figures. For example, in some cases, two blocks shown in succession can be performed substantially concurrently, or the blocks may sometimes be performed in the reverse order, depending upon the functionality involved. Also, other blocks can be added in addition to the illustrated blocks in a flowchart or block diagram.

Figure 9:
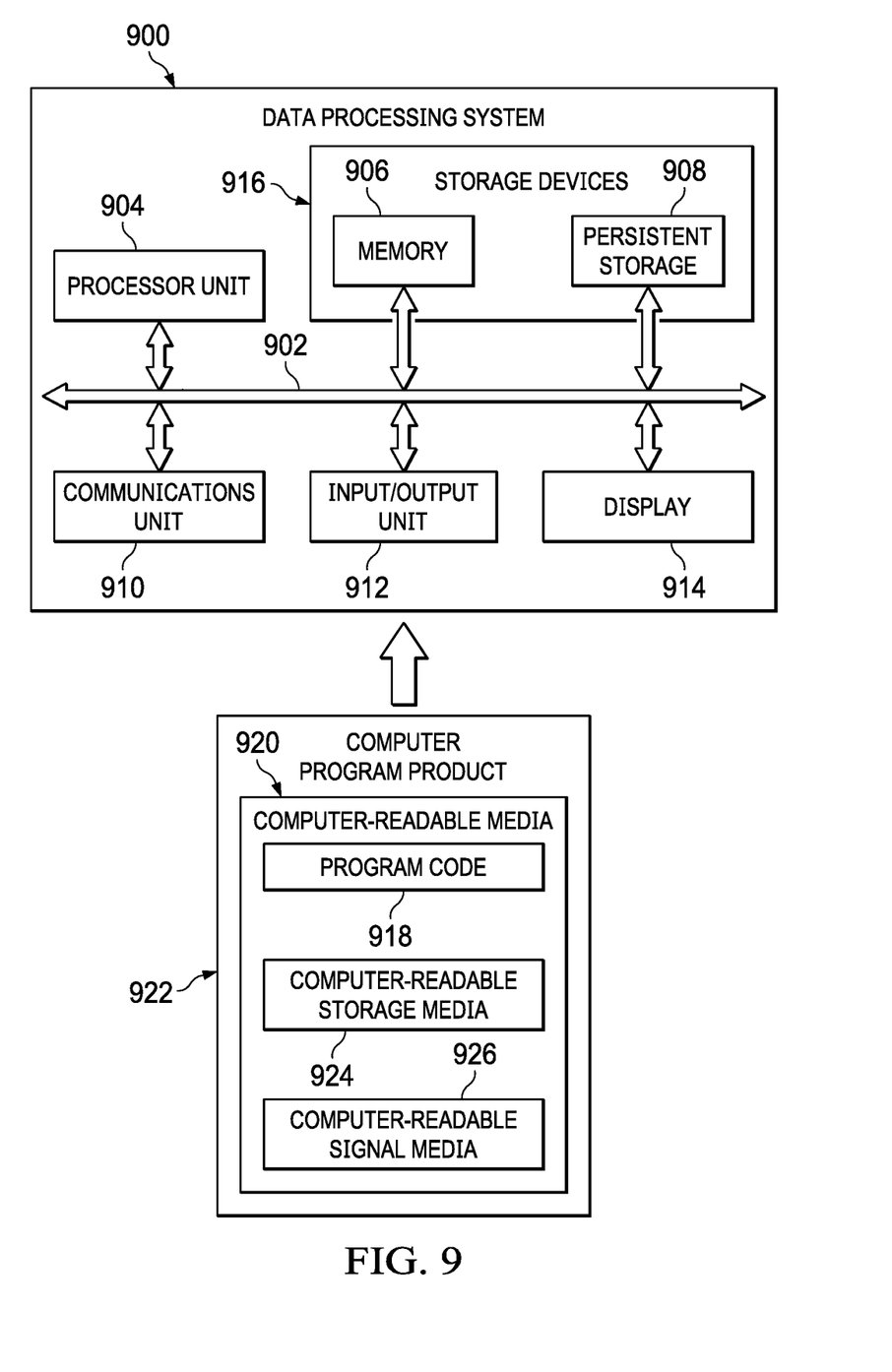
FIG. 9 is an illustration of a block diagram of a data processing system in accordance with an illustrative example.

Turning now to FIG. 9, an illustration of a block diagram of a data processing system is depicted in accordance with an illustrative example. Data processing system 900 may be used to implement computer system 148 in FIG. 1. In this illustrative example, data processing system 900 includes communications framework 902, which provides communications between processor unit 904, memory 906, persistent storage 908, communications unit 910, input/output unit 912, and display 914. In this example, communications framework 902 can take the form of a bus system.

Processor unit 904 serves to execute instructions for software that can be loaded into memory 906. Processor unit 904 can be a number of processors, a multi-processor core, or some other type of processor, depending on the particular implementation.

Memory 906 and persistent storage 908 are examples of storage devices 916. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 916 can also be referred to as computer-readable storage devices in these illustrative examples. Memory 906, in these examples, can be, for example, a random-access memory or any other suitable volatile or non-volatile storage device. Persistent storage 908 can take various forms, depending on the particular implementation.

For example, persistent storage 908 may contain one or more components or devices. For example, persistent storage 908 can be a hard drive, a solid state hard drive, a flash memory, a rewritable optical disk, a rewritable magnetic tape, or some combination of the above. The media used by persistent storage 908 also can be removable. For example, a removable hard drive can be used for persistent storage 908.

Communications unit 910, in these illustrative examples, provides for communications with other data processing systems or devices. In these illustrative examples, communications unit 910 is a network interface card.

Input/output unit 912 allows for input and output of data with other devices that can be connected to data processing system 900. For example, input/output unit 912 can provide a connection for user input through at least one of a keyboard, a mouse, or some other suitable input device. Further, input/output unit 912 can send output to a printer. Display 914 provides a mechanism to display information to a user.

Instructions for at least one of the operating system, applications, or programs may be located in storage devices 916, which are in communication with processor unit 904 through communications framework 902. The processes in the different examples can be performed by processor unit 904 using computer-implemented instructions, which can be located in a memory, such as memory 906.

These instructions are referred to as program code, computer usable program code, or computer-readable program code that can be read and executed by a processor in processor unit 904. The program code in the different examples can be embodied on different physical or computer-readable storage media, such as memory 906 or persistent storage 908.

Program code 918 is located in a functional form on computer-readable media 920 that is selectively removable and can be loaded onto or transferred to data processing system 900 for execution by processor unit 904. Program code 918 and computer-readable media 920 form computer program product 922 in these illustrative examples. In one example, computer-readable media 920 can be computer-readable storage media 924 or computer-readable signal media 926. In these illustrative examples, computer-readable storage media 924 is a physical or tangible storage device used to store program code 918 rather than a medium that propagates or transmits program code 918.

Alternatively, program code 918 may be transferred to data processing system 900 using computer-readable signal media 926. Computer-readable signal media 926 can be, for example, a propagated data signal containing program code 918. For example, computer-readable signal media 926 can be at least one of an electromagnetic signal, an optical signal, or any other suitable type of signal. These signals can be transmitted over at least one of communications links, such as wireless communications links, optical fiber cable, coaxial cable, a wire, or any other suitable type of communications link.

The different components illustrated for data processing system 900 are not meant to provide architectural limitations to the manner in which different examples may be implemented. The different illustrative examples can be implemented in a data processing system including components in addition to or in place of those illustrated for data processing system 900. Other components shown in FIG. 9 can be varied from the illustrative examples shown. The different examples can be implemented using any hardware device or system capable of running program code 918.

Thus, the illustrative examples provide one or more technical solutions that overcome a technical problem with managing medical device systems and in particular to more effectively making adjustments to the operation of a neurostimulator for deep brain stimulation.

As a result, one or more technical solutions may provide a technical effect in which a visualization is provided in a manner that enables an operator, such as a doctor or technician, to manage the operation of a medical device system, such as deep brain stimulation, more easily. One or more technical solutions provide a technical effect in the visualization that is provided through a graphical user interface that displays an augmented reality view of the medical device system with a patient in which the medical device system is implanted.

In this manner, a newer and more intuitive and efficient mechanism is provided to visualize information relating to the operation of medical devices. For example, stimulation information for a deep brain stimulation system can be displayed in a graphical user interface to provide a visualization including an augmented reality view that decreases the cognitive workload required for an operator such as a doctor managing the deep brain stimulation system. With the augmented reality view, the visualization allows the doctor to perform work more easily, intuitively, and with better focus to address the effectiveness of the treatment provided by the deep brain stimulation system, making adjustments, and performing other operations.

The description of the different illustrative examples has been presented for purposes of illustration and description and is not intended to be exhaustive or limited to the examples in the form disclosed. The different illustrative examples describe components that perform actions or operations. In an illustrative example, a component can be configured to perform the action or operation described. For example, the component can have a configuration or design for a structure that provides the component an ability to perform the action or operation that is described in the illustrative examples as being performed by the component.

Many modifications and variations will be apparent to those of ordinary skill in the art. Further, different illustrative examples may provide different features as compared to other desirable examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A visualization system for deep brain stimulation comprising:
    a camera system configured to generate images;
    a display system comprising at least one of: a projector configured to project onto a physical head of a patient, optical elements through which the head of the patient is visible, or a display device on which a visualization of the head of the patient generated from the images can be displayed; and
    an information analyzer configured to communicate with the camera system, a neurostimulator of a deep brain stimulation system, and the display system, wherein:
        the neurostimulator is configured to generate electrical signals to be sent to a group of electrodes connected to the neurostimulator;
        the information analyzer is configured to receive stimulation information from the neurostimulator, the stimulation information comprising information about an electrical signal generated by the neurostimulator and emitted by an electrode of the group of electrodes in a brain of the patient for the deep brain stimulation, wherein the stimulation information is received concurrent with emission of the electrical signal by the electrode of the group of electrodes;
        the information analyzer is configured to receive images from the camera system and identify a position of the head of the patient using the images;
        the information analyzer is configured to determine, using the position of the head of the patient, where to display information in association with the patient;
        the information analyzer is configured to display the group of electrodes for the deep brain stimulation on a live view of the head of the patient using the display system based on the position determined, such that a visualization of the group of electrodes is displayed overlaid on the live view of the head of the patient in a position corresponding to an actual position of the group of electrodes in a brain in the head of the patient;
        the information analyzer is configured to display an operation of the electrode of the group of electrodes of sending the electrical signal into the head of the patient in the visualization concurrent with delivery of the electrical signal; and
        the visualization of the operation of the electrode of the group of electrodes is displayed during a physical reaction of the patient to the deep brain stimulation such that the physical reaction of the patient to the deep brain stimulation and the operation of the electrode of the group of electrodes in the visualization overlaid on the live view of the head of the patient are both visible concurrently, wherein the live view of the head of the patient is one of: the physical head of the patient, a view through the optical elements, or the visualization of the head of the patient generated by the information analyzer from the images from the camera system and displayed on the display device.

2. The visualization system of claim 1, wherein the visualization of the operation of the electrode of the group of electrodes comprises the information analyzer displaying a graphic indicator indicating at least one of a current flow or a voltage from the electrode into the brain.

3. The visualization system of claim 1, wherein the information analyzer displays a map of the brain on the live view of the head of the patient.

4. The visualization system of claim 1 further comprising:
a sensor system for the patient, wherein the sensor system is configured to detect a group of physiological parameters for the patient, wherein the information analyzer receives the group of physiological parameters for the patient from the sensor system, and wherein the information analyzer is configured to display the information using the display system in conjunction with the live view of the head of the patient.

5. The visualization system of claim 1, wherein the information analyzer is configured to display patient information about the patient in association with the live view of the patient using the display system.

6. The visualization system of claim 5, wherein the patient information about the patient includes at least one of an image, a patient record, an x-ray, a computer aided tomography (CAT) scan, a thermal map, or a magnetic resonance imaging (MM) scan.

7. The visualization system of claim 1, further comprising a head mounted display system, wherein the display system and the camera system are located in the head mounted display system.

8. The visualization system of claim 7, wherein the information analyzer is located in the head mounted display system.

9. The visualization system of claim 1, wherein the information analyzer is configured to display the operation of the electrode of the group of electrodes of sending the electrical signal selected from at least one of a continuous signal and a pulsed signal into the head of the patient in the visualization concurrent with delivery of the electrical signal.

10. The visualization system of claim 1, wherein the visualization overlaid on the live view of the head of the patient is an augmented reality (AR) visualization.

11. The visualization system for deep brain stimulation of claim 1, wherein:
the physical reaction of the patient comprises a change in physical manifestations of a disorder being treated using the electrical signal.

12. The visualization system for deep brain stimulation of claim 1, wherein the display system is the projector, and wherein the information is overlaid on the live view of the head of the patient by projecting the information on the physical head of the patient.

13. A method for visualizing deep brain stimulation, the method comprising:
receiving, by an information analyzer, stimulation information from a neurostimulator, the stimulation information comprising information about an electrical signal generated by the neurostimulator and emitted by an electrode of a group of electrodes in a brain of a patient for the deep brain stimulation, wherein the stimulation information is received concurrent with emission of the electrical signal by the electrode of the group of electrodes;
receiving images of the patient from a camera system;
identifying a position of a head of the patient using the images;
displaying the group of electrodes on a display system based on the position determined such that a visualization of the group of electrodes is displayed overlaid on a live view of the head of the patient in a position corresponding to an actual position of the group of electrodes in the brain in the head of the patient, wherein the group of electrodes is displayed overlaid on the live view of the head of the patient concurrent with delivery of the electrical signal, and wherein the display comprises at least one of optical elements through which the head of the patient is visible or a display device on which a visualization of the head of the patient generated from the images can be displayed; and
displaying an operation of the electrode of the group of electrodes of sending the electrical signal into the head of the patient in the visualization concurrent with delivery of the electrical signal, wherein the visualization of the operation of the electrode of the group of electrodes is displayed during a physical reaction of the patient to the deep brain stimulation such that the physical reaction of the patient to the deep brain stimulation and the operation of the electrode of the group of electrodes in the visualization overlaid on the live view of the head of the patient are both visible concurrently, wherein the live view of the head of the patient is one of: a view through the optical elements or the visualization of the head of the patient generated from the images from the camera system.

14. The method of claim 13, wherein the visualization of the operation of the electrode of the group of electrodes comprises:
displaying a graphic indicator indicating at least one of a current flow or a voltage from the group of electrodes into the brain.

15. The method of claim 13 further comprising:
displaying a map of the brain on the live view of the head of the patient.

16. The method of claim 13 further comprising:
detecting a group of physiological parameters for the patient using a sensor system; and
receiving, by the information analyzer, the group of physiological parameters from the sensor system.

17. The method of claim 16 further comprising:
displaying the group of physiological parameters in association with the live view of the head of the patient on the display system.

18. The method of claim 13 further comprising:
displaying, on the display system, patient information about the patient in the visualization in association with the live view of the head of the patient.

19. The method of claim 18, wherein the patient information about the patient includes at least one of an image, a patient record, an x-ray, a computer aided tomography (CAT) scan, or a magnetic resonance imaging (MRI) scan.

20. The method of claim 13, wherein the display system and the camera system are located in a head mounted display system.

21. The method of claim 13, wherein the information analyzer is located in a head mounted display system.

22. The method of claim 13, wherein the electrical signal is selected from at least one of a continuous signal and a pulsed signal and displaying the operation of the electrode of the group of electrodes of sending the electrical signal into the head of the patient in the visualization concurrent with delivery of the electrical signal comprises displaying the operation of the electrode of the group of electrodes of sending the at least one of the continuous signal and the pulsed signal.

23. The method of claim 13, wherein information is overlaid on the head of the patient in an augmented reality (AR) visualization.

24. A visualization system for a medical device system, the visualization system comprising:
- a head mounted display system comprising:
  - a camera system configured to generate images; and
  - a display system having at least one of: optical elements through which a body of a patient is visible or a display device configured to display a visualization of the body of the patient; and
- an information analyzer configured to display the medical device system in the visualization on the display system, wherein the visualization is overlaid on a live view of the body of the patient, wherein:
  - the information analyzer is in communication with the camera system, the medical device system, and the display system;
  - the information analyzer is configured to receive images from the camera system and identify a position of the body of the patient using the images;
  - the information analyzer is configured to determine, using the position determined, where to display the visualization on the display system such that the medical device system in the visualization is displayed in a position over the live view of the body of the patient corresponding to an actual position of the medical device system in the body of the patient;
  - the information analyzer is configured to display the visualization including the medical device system on the display system such that the medical device system displayed in the visualization is overlaid on a live view of the body of the patient concurrent with an operation of the medical device system;
  - the information analyzer is configured to receive stimulation information from the medical device system, wherein the stimulation information comprises information about an electrical signal generated by the medical device system as the medical device system operates; and
  - the information analyzer is configured to display the stimulation information in the visualization on the display system such that the stimulation information is displayed in the visualization is overlaid on the live view of the body of the patient concurrent with emission of the electrical signal during the operation of the medical device system, wherein the live view of the body of the patient is one of: a visualization of the body of the patient generated from the images from the camera or a view through optical elements of the head mounted display system.

* * * * *